United States Patent [19]

Berg et al.

[11] Patent Number: 4,710,275

[45] Date of Patent: * Dec. 1, 1987

[54] SEPARATION OF ISOPROPANOL FROM T-BUTANOL BY EXTRACTIVE DISTILLATION

[76] Inventors: Lloyd Berg, 1314 S. Third Ave.; Mark G. Vosburgh, 522 W. Main St., both of Bozeman, Mont. 59715

[*] Notice: The portion of the term of this patent subsequent to Dec. 1, 2004 has been disclaimed.

[21] Appl. No.: 778,403

[22] Filed: Sep. 20, 1985

[51] Int. Cl.$^4$ .......................... B01D 3/40; C07C 29/84
[52] U.S. Cl. .......................................... 203/51; 203/56; 203/60; 203/61; 203/64; 203/65; 203/71; 568/913
[58] Field of Search ...................... 203/60, 61, 51, 56, 203/64, 65, 71; 568/918, 913

[56] References Cited

U.S. PATENT DOCUMENTS

| 2,551,584 | 5/1951 | Carlson et al. | 203/51 |
| 2,552,412 | 5/1951 | Drout et al. | 203/84 |
| 2,559,519 | 7/1951 | Smith et al. | 203/64 |
| 2,559,520 | 7/1951 | Smith et al. | 203/64 |
| 2,570,205 | 10/1951 | Carlson et al. | 203/58 |
| 2,575,243 | 11/1951 | Carlson et al. | 203/60 |
| 2,591,712 | 4/1952 | Morrell et al. | 203/84 |
| 2,591,713 | 4/1952 | Morrell et al. | 203/84 |
| 2,706,707 | 4/1955 | Morrell et al. | 203/57 |

Primary Examiner—Wilbur Bascomb

[57] ABSTRACT

Isopropanol and t-butanol cannot be separated from each other by distillation because of the proximity of their boiling points. Isopropanol can be readily separated from t-butanol by using extractive distillation in which the extractive agent is a higher boiling oxygenated organic compound or a mixture of two or more of these. Typical examples of effective agents are: methyl benzoate; methyl benzoate and hexahydrophthalic anhydride; phthalic anhydride, hexahydrophthalic anhydride and methyl benzoate.

4 Claims, No Drawings

SEPARATION OF ISOPROPANOL FROM T-BUTANOL BY EXTRACTIVE DISTILLATION

FIELD OF THE INVENTION

This invention relates to a method for separating isopropanol from t-butanol using certain higher boiling liquids as the extractive agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

Isopropanol and t-butanol are two of the most widely used alcohols in commerce today. When they are used as solvents, they frequently end up as mixtures. Whenever practical, it is mandatory to recover the solvent and re-use it.

Isopropanol and t-butanol are both manufactured by the hydration of the corresponding olefin, propylene for isopropanol and isobutylene for t-butanol. At present the propylene and isobutylene are separated to high purity before reaction with sulfuric acid and water to make the alcohol to avoid the formation of a mixture of these two alcohols in the reaction product. The usual way of recovering liquid components is by distillation in a multiplate rectification column. Isopropanol boils at 82.3° C., t-butanol at 82.5° C. and these two have a relative volatility of 1.01, making it virtually impossible to separate these two by ordinary rectification.

Extractive distillation would be an attractive method of effecting the separation of isopropanol from t-butanol if agents can be found that (1) will alter the relative volatility between isopropanol and t-butanol, (2) form no azeotrope with isopropanol or t-butanol and (3) are easy to recover from t-butanol, that is boil sufficiently above t-butanol to make separation by rectification possible with only a few theoretical plates.

Extractive distillation typically requires the addition of an equal amount to twice as much extractive agent as the isopropanol - t-butanol on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required in azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. We recommend twenty Centigrade degrees or more difference. It is also desirable that the extractive agent be miscible with the t-butanol otherwise it will form a two phase azeotrope with it and some other method of separation will have to be employed.

Smith, U.S. Pat. No. 2,559,519 described an extractive distillation process to separate n-propanol from 2-butanol using ethylene glycol butyl ether and diethylene glycol ethyl ether as extractive agents. Smith, U.S. Pat. No. 2,559,520 reported 1,3-butanediol as the extractive agent for the same separation. Carlson & Smith, U.S. Pat. No. 2,570,205 reported the use of sulfolane for the n-propanol - 2-butanol separation.

OBJECTIVE OF THE INVENTION

The object of this invention is to provide a process or method of extractive distillation that will enhance the relative volatility of isopropanol from t-butanol in their separation in a rectification column. It is a further objective of this invention to identify organic compounds which are stable, can be separated from t-butanol by rectification with relatively few plates and can be recyled to the extractive distillation column and re-used with little decomposition.

SUMMARY OF THE INVENTION

The objects of this invention are provided by a process for separating isopropanol from t-butanol which entails the use of certain oxygenated organic compounds as the agent in extractive distillation.

DETAILED DESCRIPTION OF THE INVENTION

We have discovered that certain oxygenated organic compounds, some individually but principally as mixtures, will effectively enhance the relative volatility between isopropanol and t-butanol and permit the separation of pure isopropanol from t-butanol by rectification when employed as the agent in extractive distillation. Table 1 lists methyl benzoate, its mixtures and approximate proportions that we have found to be effective. Table 2 is a similar listing for hexahydrophthalic anhydride. Table 3 lists effective extractive agents which contain methyl hexahydrophthalic anhydride; Table 4 lists methyl tetrahydrophthalic anhydride; Table 5 lists methyl salcylate and Table 6 lists three miscellaneous extractive agents.

The data in Tables 1, 2, 3, 4, 5 and 6 were obtained in a vapor-liquid equilibrium still. In each case the starting material was the 50 - 50% isopropanol - 2-butanol mixture. The ratios are the parts of extractive agent used per part of isopropanol - 2-butanol mixture. The relative volatilities are listed for each of two ratios employed. The compounds that are effective as extractive distillation agents when used alone are methyl benzoate, ethyl salicylate, hexahydrophthalic anhydride and methyl tetrahydrophthalic anhydride. The compounds which are effective when used in mixtures of two or more components are benzoic acid, cinnamic acid, salicylic acid, methyl benzoate, methyl salicylate, ethyl salicylate, benzyl benzoate, benzyl p-hydroxybenzoate, phthalic anhydride, hexahydrophthalic anhydride, methyl tetrahydrophthalic anhydride, methyl hexahydrophthalic anhydride, trimellitic anhydride and dipropylene glycol dibenzoate. The two relative volatilities shown in Tables 1-6 correspond to the two different ratios. For example in Table 4, one part of methyl tetrahydrophthalic anhydride with one part of the isopropanol - t-butanol mixture gives a relative volatility of 1.20, 6/5 parts of methyl tetrahydrophthalic anhydride gives 1.27. In Table 2, one half part of hexahydrophthalic anhydride mixed with one half part of cinnamic acid with one part of isopropanol - t-butanol mixture gives a relative volatility of 1.22, 3/5 parts of hexahydrophthalic anhydride plus 3/5 parts of cinnamic acid gives 1.28. One-third parts of hexahydrophthalic anhydride plus ⅓ parts of benzyl benzoate plus ⅓ parts of benzoic acid mixed with one part of isopropanol - 2-butanol mixture gives a relative volatility of 1.23, with 2/5 parts, these three give 1.24. In every example in Tables 1-6, the starting material is a 50 - 50% mixture of isopropanol - t-butanol which possesses a relative volatility of 1.01.

TABLE 1
Extractive Agents Which Contain Methyl Benzoate

| Compounds | Ratios | | Relative Volatilities | |
|---|---|---|---|---|
| None | — | | 1.01 | |
| Methyl benzoate | 1 | 6/5 | 1.13 | 1.13 |
| Methyl benzoate, Benzoic acid | $(\frac{1}{2})^2$ | $(3/5)^2$ | 1.06 | 1.14 |
| Methyl benzoate, Cinnamic acid | " | " | 1.20 | 1.10 |
| Methyl benzoate, Ethyl salicylate | " | " | 1.15 | 1.15 |
| Methyl benzoate, Phthalic anhydride | " | " | 1.17 | 1.18 |
| Methyl benzoate, Salicylic acid | " | " | 1.13 | 1.09 |
| Methyl benzoate, Salicylic acid, Cinnamic acid | $(\frac{1}{3})^3$ | $(2/5)^3$ | 1.11 | 1.14 |
| Methyl benzoate, Salicylic acid, Ethyl salicylate | " | " | 1.15 | 1.10 |

TABLE 2
Extractive Agents Which Contain Hexahydrophthalic Anhydride.

| Compounds | Ratios | | Relative Volatilities | |
|---|---|---|---|---|
| Hexahydrophthalic anhydride (HHPhAn) | 1 | 6/5 | 1.12 | 1.17 |
| HHPhAn, Benzoic acid | $(\frac{1}{2})^2$ | $(3/5)^2$ | 1.17 | 1.23 |
| HHPhAn, Benzyl benzoate | " | " | 1.07 | 1.15 |
| HHPhAn, Benzyl p-hydroxybenzoate | " | " | 1.10 | 1.21 |
| HHPhAn, Cinnamic acid | " | " | 1.22 | 1.28 |
| HHPhAn, Ethyl salicylate | " | " | 1.13 | 1.12 |
| HHPhAn, Methyl benzoate | " | " | 1.21 | 1.22 |
| HHPhAn, Methyl salicylate | " | " | 1.19 | 1.21 |
| HHPhAn, Salicylic acid | " | " | 1.19 | 1.24 |
| HHPhAn, Benzoic acid, Benzyl benzoate | $(\frac{1}{3})^3$ | $(2/5)^3$ | 1.12 | 1.06 |
| HHPhAn, Benzoic acid, Methyl salicylate | " | " | 1.11 | 1.14 |
| HHPhAn, Methylbenzoate, Ethyl salicylate | " | " | 1.17 | 1.27 |
| HHPhAn, Methylbenzoate, Phthalic anhydride | " | " | 1.25 | 1.28 |
| HHPhAn, Benzyl benzoate, Benzyl p-OH benzoate | " | " | 1.10 | 1.19 |
| HHPhAn, Benzyl benzoate, Benzoic acid | " | " | 1.23 | 1.24 |

TABLE 2-continued
Extractive Agents Which Contain Hexahydrophthalic Anhydride.

| Compounds | Ratios | | Relative Volatilities | |
|---|---|---|---|---|
| HHPhAn, Benzyl benzoate, Cinnamic acid | " | " | 1.25 | 1.28 |
| HHPhAn, Benzyl benzoate, Methyl tetrahydrophthalic anhydride | " | " | 1.14 | 1.20 |
| HHPhAn, Methyl benzoate, Phthalic anhydride, Benzyl p-hydroxybenzoate | $(\frac{1}{4})^4$ | $(\frac{1}{4})^4$ | 1.12 | 1.14 |

TABLE 3
Extractive Agents Which Contain Methyl Hexahydrophthalic Anhydride.

| Compounds | Ratios | | Relative Volatilities | |
|---|---|---|---|---|
| MeHHPhAn, Benzoic acid | $(\frac{1}{2})^2$ | $(3/5)^2$ | 1.22 | 1.26 |
| MeHHPhAn, Benzyl benzoate | " | " | 1.25 | 1.13 |
| MeHHPhAn, Methyl benzoate | " | " | 1.13 | 1.13 |
| MeHHPhAn, Salicylic acid | " | " | 1.18 | 1.20 |
| MeHHPhAn, Benzoic acid, Benzyl benzoate | $(\frac{1}{3})^3$ | $(2/5)^3$ | 1.11 | 1.20 |
| MeHHPhAn, Cinnamic acid, Methyl salicylate | " | " | 1.08 | 1.10 |
| MeHHPhAn, Cinnamic acid, Methyl salicylate | " | " | 1.06 | 1.16 |
| MeHHPhAn, Methyl salicylate, Trimellitic anhydride | " | " | 1.21 | 1.24 |

TABLE 4
Extractive Agents Which Contain Methyl Tetrahydrophthalic Anhydride

| Compounds | Ratios | | Relative Volatilities | |
|---|---|---|---|---|
| Methyl tetrahydrophthalic anhydride (MeTHPhAn) | 1 | 6/5 | 1.20 | 1.27 |
| MeTHPhAn, Benzyl benzoate | $(\frac{1}{2})^2$ | $(3/5)^2$ | 1.10 | 1.17 |
| MeTHPhAn, Dipropylene glycol dibenzoate | " | " | 1.12 | 1.09 |
| MeTHPhAn, Methyl salicylate | " | " | 1.05 | 1.19 |
| MeTHPhAn, Methyl benzoate, Benzyl p-OH benzoate | $(\frac{1}{3})^3$ | $(2/5)^3$ | 1.23 | 1.26 |
| MeTHPhAn, Methyl benzoate, Cinnamic acid | " | " | 1.21 | 1.29 |
| MeTHPhAn, Methyl benzoate, Dipropylene glycol dibenzoate | " | " | 1.11 | 1.08 |

TABLE 5
Extractive Agents Which Contain Methyl Salicylate.

| Compounds | Ratios | | Relative Volatilities | |
|---|---|---|---|---|
| Methyl salicylate, Trimellitic anhydride | $(\frac{1}{2})^2$ | $(3/5)^2$ | 1.28 | 1.19 |
| Methyl salicylate, Cinnamic acid | " | " | 1.13 | 1.14 |
| Methyl salicylate, Cinnamic acid, Trimellitic anhydride | $(\frac{1}{3})^3$ | $(2/5)^3$ | 1.18 | 1.18 |
| Methyl salicylate, Benzyl benzoate, Benzyl p-OH benzoate | " | " | 1.10 | 1.12 |

TABLE 6
Miscellaneous Extractive Agents

| Compounds | Ratios | | Relative Volatilities | |
|---|---|---|---|---|
| Ethyl salicylate | 1 | 6/5 | 1.07 | 1.13 |
| Benzyl benzoate, Benzoic acid | $(\frac{1}{2})^2$ | $(3/5)^2$ | 1.08 | 1.08 |
| Benzyl benzoate, Trimellitic anhydride | " | " | 1.24 | 1.27 |

TABLE 7

| Agent | Time min. | Stillpot At Start | Temp. °C. Sampling | Overhead Temp. When Sampling | Weight % Overhead | Isopropanol Bottoms | Relative Volatility |
|---|---|---|---|---|---|---|---|
| Methyl | 60 | 81.6 | 100.6 | 77.4 | 65.9 | 55.8 | 1.10 |
| benzoate, | 90 | 81.6 | 118.6 | 76.8 | 60.9 | 44.8 | 1.16 |
| HHPhAn | | | | | | | |
| Methyl | 50 | 85.2 | 111.8 | 78.8 | 62.9 | 52.5 | 1.10 |
| benzoate, | 80 | 85.2 | 125.0 | 77.2 | 57.3 | 38.3 | 1.19 |
| HHPhAn, | | | | | | | |
| Phthalic anh. | | | | | | | |

| Notes: Agent | Feed, % isopropanol | Agent Flow ml/min. | Boilup Rate ml/min. | Agent Temp. | Agent Comp., Weight % |
|---|---|---|---|---|---|
| Methyl benzoate, HHPhAn | 50 | 20 | 10–20 | 70–80 | 50% Methyl benzoate |
| Methyl benzoate, HHPhAn, Phthalic anh. | 50 | 20 | 10–20 | 70–80 | 50% MeBenz 30% HHPhAn 20% Phthalic anh. |

Several of the compounds listed in Table 1–6 and whose relative volatility had been determined in the vapor-liquid equilibrium still, were then evaluated in a glass perforated plate rectification column possessing 4.5 theoretical plates. The results are listed in Table 7. The isopropanol - t-butanol mixture used contained 50% isopropanol. The first run is with methyl benzoate and hexahydrophthalic anhydride as the extractive agent and here a relative volatilty of 1.16 is obtained. This compares with 1.21 and 1.22 shown for hexahydrophthalic anhydride and methyl benzoate in Table 2, the data for which was obtained in the vapor-liquid equilibrium still. The second run is with a mixture comprising 50% methyl benzoate, 30% hexahydrophthalic anhydride and 20% phthalic anhydride. This agent gives a relative volatility of 1.19 which may be compared with values of 1.25 and 1.28 in Table 2.

THE USEFULNESS OF THE INVENTION

The usefulness or utility of this invention can be demonstrated by referring to the data presented in Tables 1–7. All of the successful extractive distillation agents show that isopropanol can be removed from t-butanol by means of distillation in a rectification column and that the ease of separation as measured by relative volatility is considerable. Without these extractive distillation agents, virtually no improvement will occur in the rectification column. The data also show that the most attractive agents will operate at a boilup rate low enough to make this a useful and efficient method of recovering high purity isopropanol from any mixture with t-butanol. The stability of the compounds used and the boiling point difference is such that complete recovery and recycle is obtainable by a simple distillation and the amount required for make-up is small.

WORKING EXAMPLES

Example 1 Twenty-five grams of isopropanol, 25 grams of t-butanol and fifty grams of methyl benzoate were charged to an Othmer type glass vapor-liquid equilibrium still and refluxed for three hours. Analysis of the vapor and liquid by gas chromatography gave a vapor composition of 61.9% isopropanol, 38.5% t-butanol; a liquid composition of 59% isopropanol, 41% t-butanol. This indicates a relative volatility of 1.13. Ten grams of methyl benzoate were added and refluxing continued for another nine hours. Analysis indicatod a vapor composition of 62.1% isopropanol, 37.9% t-butanol; a liquid composition of 59.1% isopropanol, 40.9% t-butanol which is a relative volatility of 1.13.

EXAMPLE 2

Fifty grams of the isopropanol - t-butanol mixture, 25 grams of hexahydrophthalic anhydride and 25 grams of methyl benzoate were charged to the vapor-liquid equilibrium still and refluxed for 15 hours. Analysis indicated a vapor composition of 54.8% isopropanol, 45.2% t-butanol; a liquid composition of of 50% isopropanol, 50% t-butanol which is a relatve volatility of 1.21. Five grams of hexahydrophthalic anhydride and five grams of methyl benzoate were added and refluxing continued for another eight hours. Analysis indicated a vapor composition of 52.6% isopropanol, 47.4% t-butanol; a liquid composition of 47.8% isopropanol, 52.2% t-butanol which is a relative volatility of 1.22.

EXAMPLE 3

Fifty grams of the isopropanol - t-butanol mixture, 17 grams of cinnamic acid, 17 grams of methyl tetrahydrophthalic anhydride and 17 grams of methyl benzoate were charged to the vapor-liquid equilibrium still and refluxed for 12 hours. Analysis indicated a vapor composition of 57.2% isopropanol, 42.8% t-butanol; a liquid composition of 52.6% isopropanol, 47.4% t-butanol which is a relative volatility of 1.21. Three grams each of cinnamic acid, methyl tetrahydrophthalic anhydride and methyl benzoate were added and refluxing continued for another ten hours. Analysis indicated a vapor composition of 55.6% isopropanol, 44.4% t-butanol and a liquid composition of 49.1% isopropanol, 50.9% t-butanol which is a relative volatility of 1.29.

EXAMPLE 4

A glass perforated plate rectification column was calibrated with ethylbenzene and p-xylene which possesses a relative volatilty of 1.06 and found to have 4.5 theoretical plates. A solution of 200 grams of isopropanol and 200 grams of t-butanol was placed in the stillpot and heated. When refluxing began, an extractive agent consisting of 50% methyl benzoate and 50% hexahydrophthalic anhydride was pumped into the column at a rate of 20 ml/min. The temperature of the extractive agent as it entered the column was 70°–80° C. After establishing the feed rate of the extractive agent, the heat input to the isopropanol -t-butanol in the stillpot was adjusted to give a reflux rate of 10–20 ml/min. After one hour of operation, overhead and bottoms samples of approximately two ml. were collected and analysed by gas chromatography. The overhead analysis was 65.9% isopropanol, 34.1% t-butanol. The bottoms analysis was 55.8% isopropanol, 44.2% t-butanol. Using these compositions in the Fenske equation, with the number of theoretical plates in the column being 4.5, gave an average relative volatility of 1.10 for each theoretical plate. After 1.5 hours of total operating time, the overhead and bottoms samples were again taken and analysed. The overhead composition was 60.9% isopropanol, 39.1% t-butanol and the bottoms composition was 44.8% isopropanol, 55.2% t-butanol. This gave an average relative volatility of 1.16 for each theoretical plate.

EXAMPLE 5

A solution of 200 grams of isopropanol and 200 grams of t-butanol was placed in the stillpot of the same column used in Example 4 and heat applied. When refluxing began, an extractive agent comprising 50% methyl benzoate, 30% hexahydrophthalic anhydride and 20% phthalic anhydride was fed to the top of the column at a feed rate of 20 ml/min. and a temperature of 70°–80° C. After establishing the feed rate of the extractive agent, the heat input to the isopropanol - t-butanol in the stillpot was adjusted to give a total reflux rate of 10–20 ml/min. Having established the reflux rate, the column was allowed to operate for 50 minutes. After 50 minutes of steady operation, overhead and bottoms samples of approximately two ml. were collected and analysed by gas chromatography. The overhead analysis was 62.9% isopropanol, 37.1% t-butanol and the bottoms analysis was 52.5% isopropanol, 47.5% t-butanol. Using these compositions in the Fenske equation with the number of theoretical plates in the column being 4.5, gave an average relative volatility of 1.10 for each theoretical plate. After 1.5 hours of total operation, the overhead and bottoms were again taken and analysed. The overhead composition was 57.3% isopropanol, 42.7% t-butanol and the bottoms composition was 38.3% isopropanol, 61.7% t-butanol. This gave an average relative volatility of 1.19 for each theoretical plate.

What is claimed is:

1. A method for recovering isopropanol from a mixture of isopropanol and t-butanol which comprises distilling a mixture of isopropanol and t-butanol in a rectification column in the presence of about one to two parts of extractive agent per part of isopropanol - t-butanol mixture, recovering essentially pure isopropanol as overhead product, obtaining the t-butanol and the extractive agent from the stillpot or reboiler, separating the t-butanol from the extractive agent by conventional distillation in another rectification column, wherein said extractive agent
   (1) is an organic compound or a mixture of organic compounds composed solely of carbon, hydrogen and oxygen and containing a six carbon atom aromatic ring
   (2) boils at least 100 Centigrade degrees above t-butanol
   (3) does not form binary azeotropes with either isopropanol or t-butanol
   (4) does not form a ternary azeotrope with isopropanol and t-butanol
   (5) is soluble in boiling isopropanol - t-butanol mixtures
   (6) in combination with isopropanol and t-butanol, results in a relative volatility of isopropanol to t-butanol greater than 1.10.

2. The process of claim 1 wherein the extractive agent in combination with isopropanol and t-butanol results in a relative volatility of isopropanol to t-butanol in the range of about 1.11 to 1.30.

3. The process of claim 1 wherein the extractive agent is selected from a member of the group consisting of methyl benzoate, ethyl salicylate, hexahydrophthalic anhydride and methyl tetrahydrophthalic anhydride.

4. The process of claim 1 wherein the extractive agent is selected from mixtures consisting of at least two compounds from the group consisting of benzoic acid, cinnamic acid, salicylic acid, methyl benzoate, methyl salicylate, ethyl salicylate, benzyl benzoate, benzyl p-hydroxybenzoate, phthalic anhydride, hexahydrophthalic anhydride, methyl tetrahydrophthalic anhydride, methyl hexahydrophthalic anhydride, trimellitic anhydride and dipropylene glycol dibenzoate.

* * * * *